United States Patent [19]

Minato

[11] Patent Number: 4,811,251

[45] Date of Patent: Mar. 7, 1989

[54] VESSEL OPENING TOP INSPECTION METHOD

[75] Inventor: Nobuhiro Minato, Tokyo, Japan

[73] Assignee: Toyo Glass Company Limited, Tokyo, Japan

[21] Appl. No.: 831,692

[22] Filed: Feb. 21, 1986

[30] Foreign Application Priority Data

Feb. 22, 1985 [JP] Japan ............................... 60-32900

[51] Int. Cl.$^4$ ............................................. G01N 21/90
[52] U.S. Cl. ..................................... 364/552; 364/507; 356/240; 250/223 B
[58] Field of Search ................ 364/507, 552; 356/240, 356/237; 209/522, 524, 526; 250/223 B; 358/106; 73/637, 638

[56] References Cited

U.S. PATENT DOCUMENTS

| | | | |
|---|---|---|---|
| 4,488,648 | 12/1984 | Claypool | 364/507 |
| 4,498,003 | 2/1985 | Cibis | 356/240 |
| 4,606,635 | 8/1986 | Miyazawa et al. | 356/240 |
| 4,650,326 | 3/1987 | Nagamine et al. | 356/240 |

Primary Examiner—Parshotam S. Lall
Assistant Examiner—Ellis B. Ramirez
Attorney, Agent, or Firm—Sughrue, Mion, Zinn, Macpeak and Seas

[57] ABSTRACT

A vessel opening top inspection apparatus which can accurately detect presence or absence of an overpress finish of a vessel such as a bottle. The apparatus comprises a projector, an image sensor, a memory, a top detecting means including a top width detecting means and a width judging means, and an overpress finish detecting means. Light projected by the projector and reflected from an opening top of a vessel in position for inspection is received by the image sensor outputs of cells of which are stored as digital amounts individually into cells of the memory specified by corresponding addresses whereafter the digital amounts are judged one after another to detect the opening top and then the digital amounts are judged one after another for addresses after such detection to detect presence or absence of an overpress finish on the vessel depending upon the magnitude of the digital amounts.

1 Claim, 11 Drawing Sheets

VESSEL OPENING TOP INSPECTION METHOD

BACKGROUND OF THE INVENTION

This invention relates to a vessel opening top inspection apparatus for inspecting presence or absence of a defect at an opening top of a vessel such as a bottle.

One inspection apparatus of the type mentioned has been already proposed by the applicant of the present patent application and is disclosed in Japanese laid-open pat. No. 59-65243. The apparatus comprises a projector for projecting light toward an opening top of a bottle, a single photoelectric transducer element for receiving light reflected from the opening top of the bottle to output an electric signal of a level corresponding to an amount of the light received, bottle rotating means for rotating the bottle to allow light from the projector to be projected over an entire circumference of the opening top of the bottle, an amplifier for amplifying the output signal of the photoelectric transducer element, the amplifier being adjustable with its amplification degree, a memory for storing an output signal of the amplifier for each bottle, operation controlling means for determining an average of data for a predetermined number of last bottles from among data stored in the memory and for adjusting the amplification degree of the amplifier so as to coincide with a predetermined value, and comparing means for comparing output signals of the amplifier for the entire circumference of the opening top of a bottle for inspection and for outputting a defect signal when an extraordinary component of the output signal of the amplifier exceeds a predetermined value.

Figure 2:
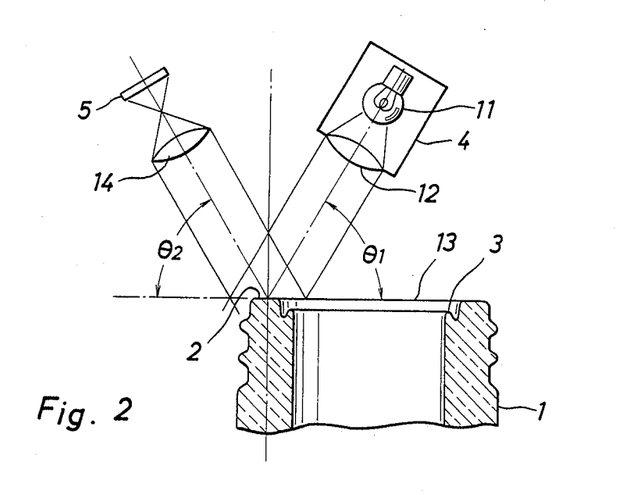
FIG. 2 is a schematic illustration showing an arrangement of a projector and a linear image sensor for inspecting a bottle according to an embodiment of the invention.
Figure 3:
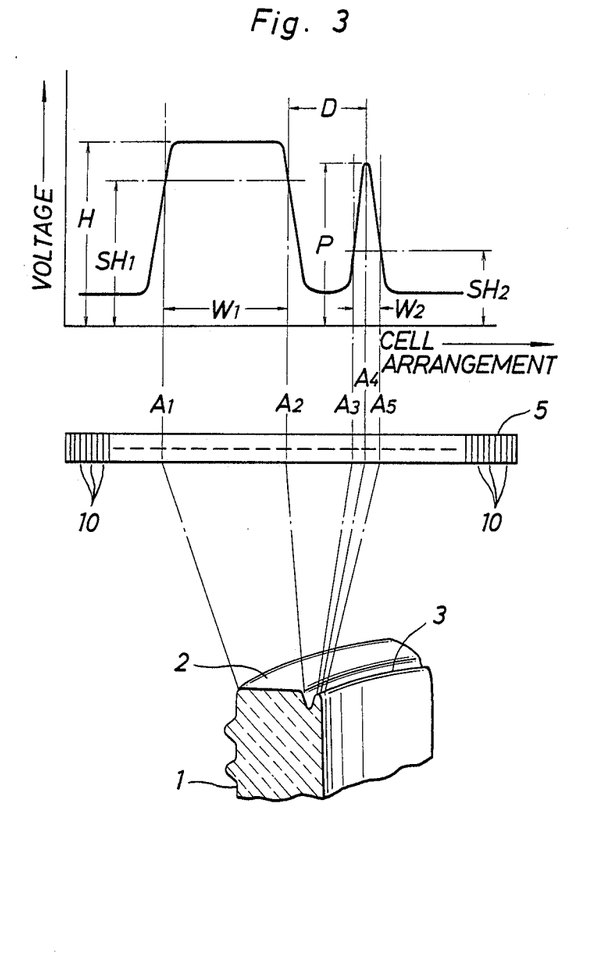
FIG. 3 is a schematic illustration showing a shape of an opening top of a bottle, an arrangement of cells of the linear image sensor and outputs of the cells.

However, while the apparatus can detect a defect formed on an opening top of a bottle where the defect is a hollow or depression such as a warp or dip finish and a line over finish which is concave at part of a circumference of the opening top of the bottle and will damage the closure of the bottle, such an overpress finish 3 as seen in FIGS. 2 and 3 which is formed to project annularly along an inner circumference of an opening top 2 of a bottle 1 cannot be detected.

Such an overpress finish 3 may be broken and drop into the bottle and mixed with contents when the opening of the bottle is closed with a crown, a threaded cap or the like. Accordingly, the overpress finish is a most significant drawback.

SUMMARY OF THE INVENTION

It is an object of the present invention to provide a vessel opening top inspection apparatus which can accurately detect presence or absence of an overpress finish of a bottle.

Figure 1:
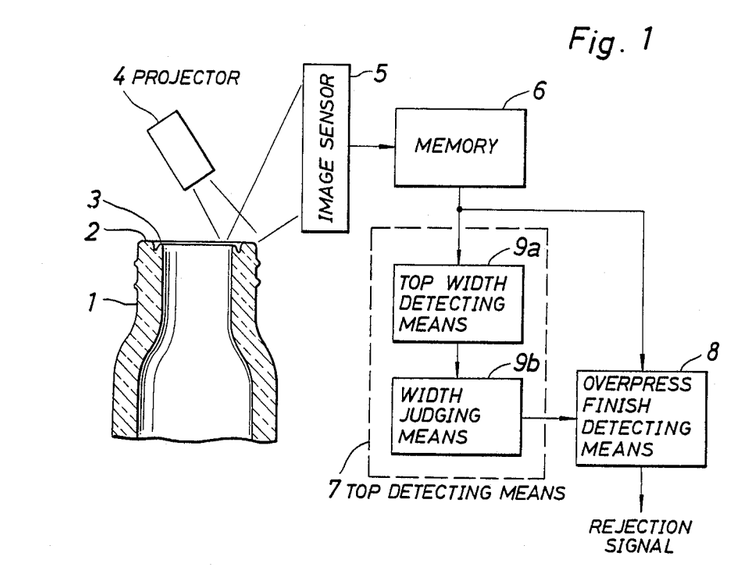
FIG. 1 is a block diagram illustrating general construction of a vessel opening top inspection apparatus according to the present invention.

An apparatus of the present invention comprises, as generally shown in FIG. 1, a projector 4, an image sensor 5, a memory 6, a top detecting means 7, and an overpress finish detecting means 8.

The projector 4 projects light toward an opening top 2 of a vessel such as a bottle 1.

The image sensor 5 is disposed to receive light reflected from the bottle 1 over a predetermined range including the full width of the opening top 2 of the bottle 1 as shown in FIG. 3.

Relations among light from the bottle 1, an arrangement of cells 10 of the image sensor 5 (a linear type one is shown) and output voltages (analog amount) of the cells 10 are illustrated in FIG. 3.

The memory 6 stores outputs of the cells 10 of the image sensor 5 as digital amounts individually in cells of corresponding addresses thereof.

The top detecting means 7 judges the digital amounts stored in the memory 6 in a predetermined order of the addresses of the memory 6 to detect a top of a bottle.

The overpress finish detecting means 8 judges, after detecting of a top of a bottle by the top detecting means 7, the digital amounts stored in the memory 6 one after another to detect presence or absence of an overpress finish 3.

The top detecting means 7 may preferably include a top width detecting means 9a and a width judging means 9b.

The top width detecting means 9a judges the digital amounts stored in the memory 6 one after another either in an order of the addresses of the memory 6 in a direction from the outside toward the inside of the opening top 2 of the bottle 1 or in the reverse order to determine a width $W_1$ of the opening top 2 from a difference from an address for which the digital amount first exceeds a threshold $SH_1$ as in FIG. 3 to another address for which the digital amount becomes smaller than the threshold $SH_1$ again. In other words, a width $W_1$ is calculated when the height H of the opening top 2 is higher than the threshold $SH_1$.

The width judging means 9b judges if the width $W_1$ detected by the top width detecting means 9a is greater than a predetermined value or not.

Accordingly, after an opening top of a vessel such as a bottle has been detected, it is judged if there is an overpress finish around a circumference of the vessel.

DETAILED DESCRIPTION OF THE PREFERRED EMBODIMENT

Now, an embodiment of the present invention will be described in detail with reference to the drawings.

In the embodiment shown, light from a lamp 11 of a projector 4 is condensed by a lens 12 and is then projected obliquely toward an opening top 2 of a bottle 1 from above and outwardly from the inside of an opening 13 of the bottle 1 as shown in FIG. 2. Light reflected from the opening top 2 passes through a lens 14 located at a symmetrical position outside an opening range of the bottle 1 relative to the position of the projector 4 and is received by a known linear image sensor 5. An angle $\theta_1$ (incident angle) of an axis of the projected light and an angle $\theta_2$ (angle of reflection) of the received light both relative to the opening top 2 are preferably 60 to 80 degrees.

The linear image sensor 5 includes up to, for example, 2048 cells 10 (2048 picture elements) of the CCD type or the MOS type arranged in a row in a direction of the width of the opening top 2 as shown in FIG. 3 and is disposed to receive reflected light from the bottle 1 over a predetermined range including the width of the opening top 2.

Thus, light reflected from a convex portion of the the opening top 2 of the bottle 1 is bright while light reflected from a concave portion is dark. Accordingly, output voltages of the cells 10 of the image sensor 5 will present values corresponding to degrees of unevenness of the opening top 2, and illustrative representation of such output voltages in a series of analog amounts will be such as shown in FIG. 3.

Figure 4:
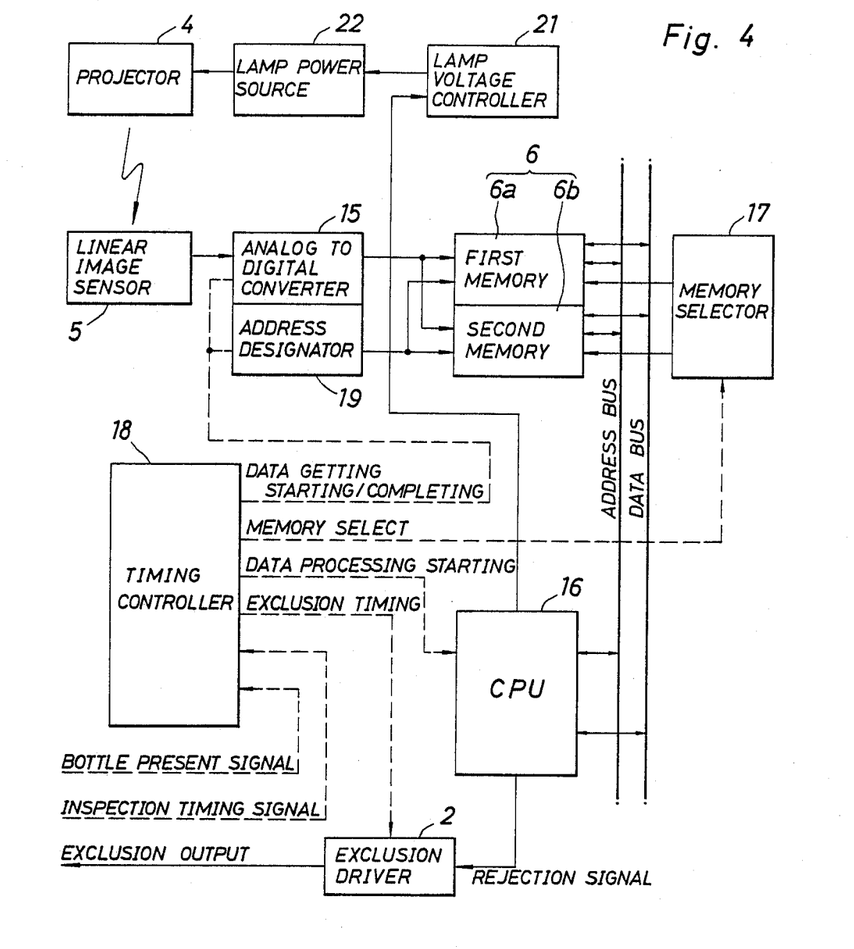
FIG. 4 is a block diagram illustrating general construction of the entire vessel opening top inspection apparatus.

The cells 10 of the linear image sensor 5 are scanned one after another, and output voltages of the cells 10 are individually converted into digital amounts (hereinafter referred to as data) by an analog to digital converter 15 such as shown in FIG. 4.

The bottle 1 is fed to an inspection position as shown in FIG. 2 by means of a conveyor or the like and is rotated at least one complete rotation by a known bottle rotating means (not shown) so as to be inspected by the present inspection apparatus. Thus, if the bottle 1 is determined as an acceptable product, then it is transported to another place by means of a conveyor or the like. On the contrary if it is determined as a rejected product, it is excluded. Getting (conversion into digital amounts) and processing of data and timings thereof are all controlled by a microcomputer. It is to be noted that a bottle 1 may otherwise be inspected either while it is temporarily stopped at a fixed position or while it is being moved without being rotated.

The microcomputer includes a central processing unit (CPU) 16, a pair of first and second memories 6a and 6b, a memory selector 17, a timing controller 18, an address designator 19 and so on.

The first and second memories 6a and 6b are controlled by the memory selector 17 such that a writing operation and a reading operation are alternately conducted therewith. Thus, when data taken in by the analog to digital converter 15 are stored into one of the memories 6a and 6b, data stored in the other memory 6a or 6b are read out therefrom and processed by the CPU 16. Data from the analog to digital converter 15 are stored into those cells of the memory 6a or 6b designated by the address designator 19 corresponding to the individual cells 10 of the linear image sensor 5.

Figures 5, 7:
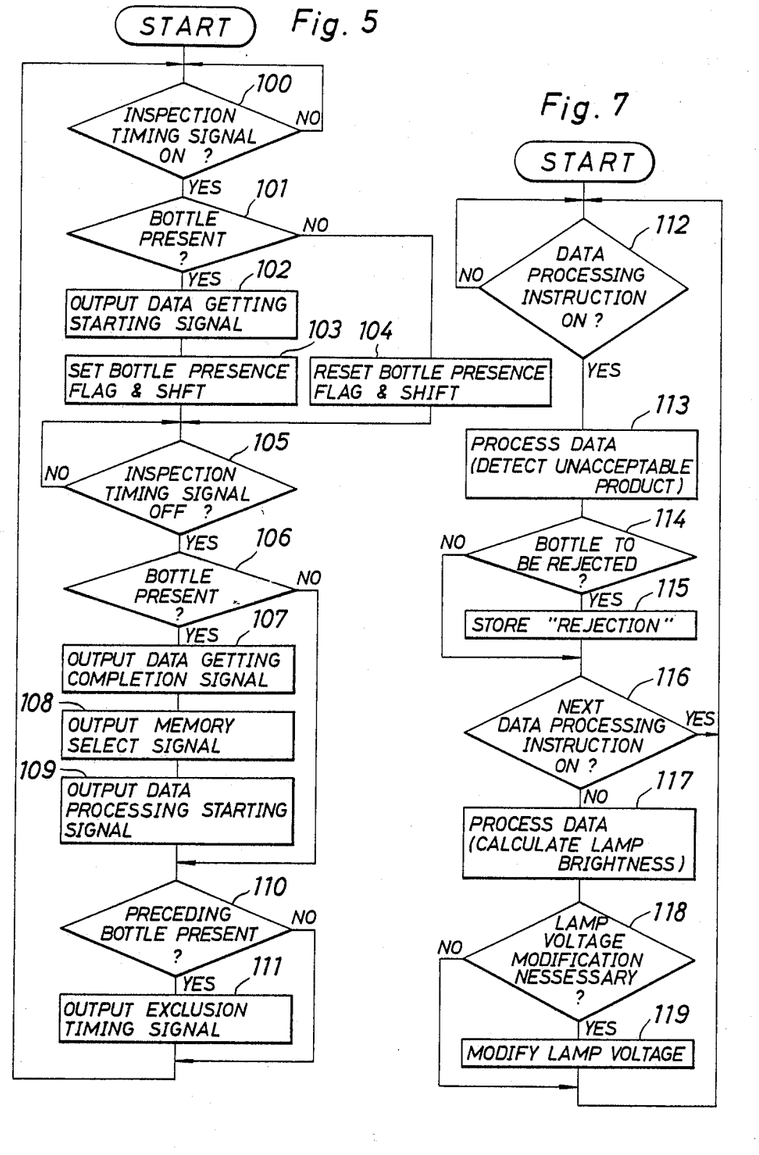
FIG. 5 is a flow chart illustrating operations of a timing controller of the apparatus of FIG. 4.
FIG. 7 is a flow chart illustrating an outline of data processing by a central processing unit of the apparatus of FIG. 4.
Figure 6:
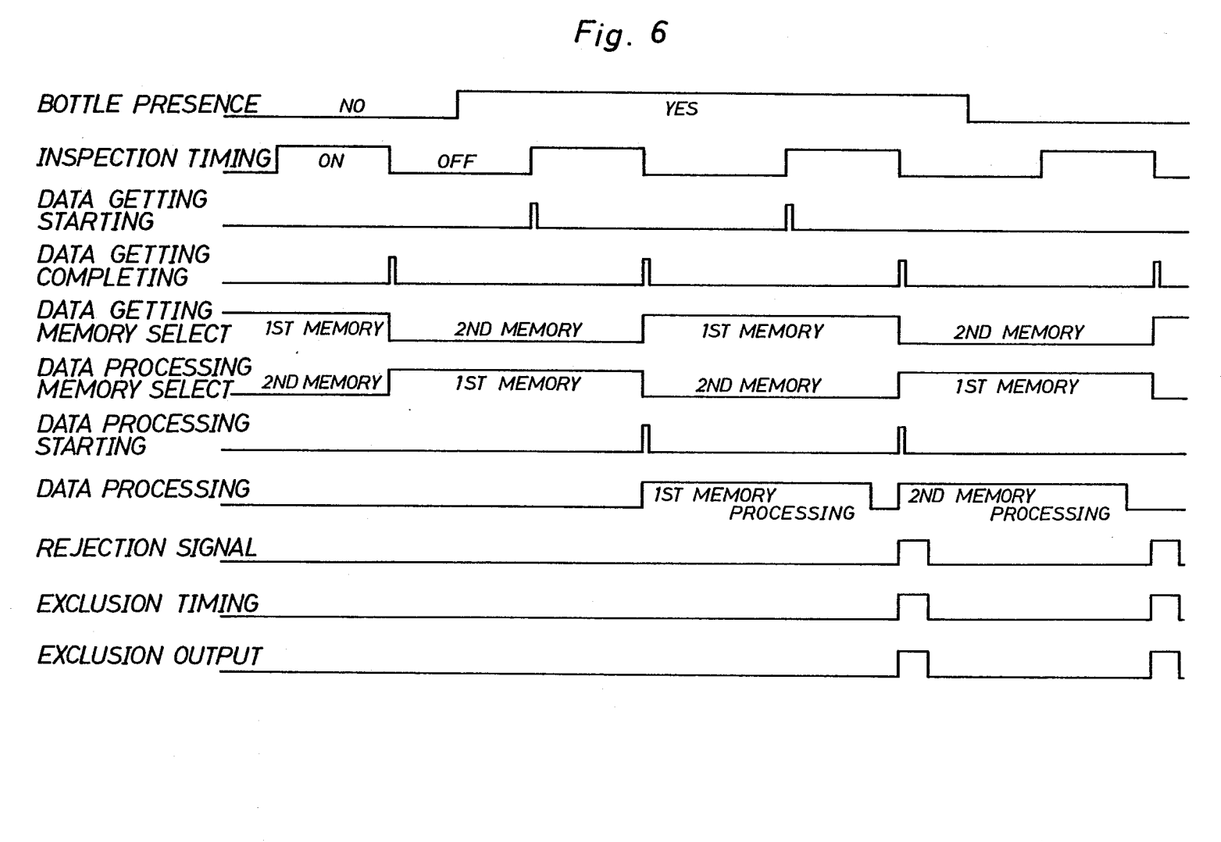
FIG. 6 is a time chart illustrating the operations of the timing controller of FIG. 4.

The timing controller 18 receives two external signals including a bottle presence signal (FIG. 6) from a bottle detector (not shown) which detects if there is a bottle 1 at the inspection position or not, and an inspection timing signal (FIG. 6) from an inspection signal generator (not shown), and outputs, in response to the two signals received, various signals as illustrated in a time chart of FIG. 6 in an order as illustrated in a flow chart of FIG. 5.

In particular, referring to FIG. 5, if an inspection timing signal is inputted, this is tested at step 100 . . . is an inspection timing signal on ? and if the results of the test are YES, then control goes to step 101 . . . is a bottle present ?

If the results of the test at step 101 are YES, then control advances to step 102 . . . output a data getting starting signal. The data getting starting signal thus outputted is received by the analog to digital converter 15 and the address designator 19 to effect getting of data in the manner described above. After then, control goes to step 103 . . . set a bottle presence flag and shift. On the other hand, if the results of the test at step 101 is NO, then control goes to step 104 . . . reset a bottle presence flag and shift. After steps 103 and 104, a test of step 105 . . . is an inspection timing signal off ? is effected, and here if the results are YES, then it is followed by step 106 . . . is a bottle present ? If the results are YES here, control goes to step 107 . . . output a data getting completion signal thereby completing the required getting of the data. Then, control goes to step 108 . . . output a memory selection signal. The memory selection signal is inputted to the memory selector 17 to control writing and reading operations of the first and second memories 6a and 6b in a manner as described above. This is followed by step 109 . . . output a data processing starting signal. The data processing starting signal is inputted to the CPU 16. After then, testing of step 110 . . . is the preceding bottle present ? is effected. Meanwhile, if the results of the test at step 106 aer NO, it is followed directly by step 110 without passing the steps 107, 108 and 109. If the results of the test at step 110 are YES, it is followed by step 111 . . . output an exclusion timing signal. The exclusion timing signal is inputted to an exclusion driver 20 of FIG. 4. After then, control returns to step 100 to repeat such a sequence of operations as described above.

If a data processing starting signal is inputted to the CPU 16 from the timing controller 18 as described above, data recalled from the first or second memory 6a or 6b are processed by the CPU 16. Such processing operations will be first described generally with reference to a flow chart of FIG. 7. At first, testing of step 112 . . . is a data processing instruction ON ? is effected, and if here the results are YES, control goes to step 113 . . . process the data (detect an unacceptable product)

so that presence or absence of an overpress finish 3 on an opening top 2 of the bottle 1 may be detected in a manner as hereinafter described. After then, a test of step 114 . . . is the bottle to be rejected ? is effected, and if the results are YES, operation of step 115 ... store "rejection" follows, whereafter testing of step 116 ... is a next data processing instruction on? is effected. If the results are affirmative, control returns to step 112, but on the contrary if in the negative, control goes to step 117 ... process the data (calculate brightness of a lamp)

so that the brightness of light from the projector 4 is calculated. This is followed by a test of step 118 ... correction of a lamp voltage necessary? and if the results of the test are YES, control goes to step 119 ... correct a lamp voltage so that a signal corresponding to an amount to be corrected is inputted to a lamp voltage controller 21 from the CPU 16 to control a lamp power source 22 to adjust the brightness of the lamp 11 of the projector 4.

Figure 8:
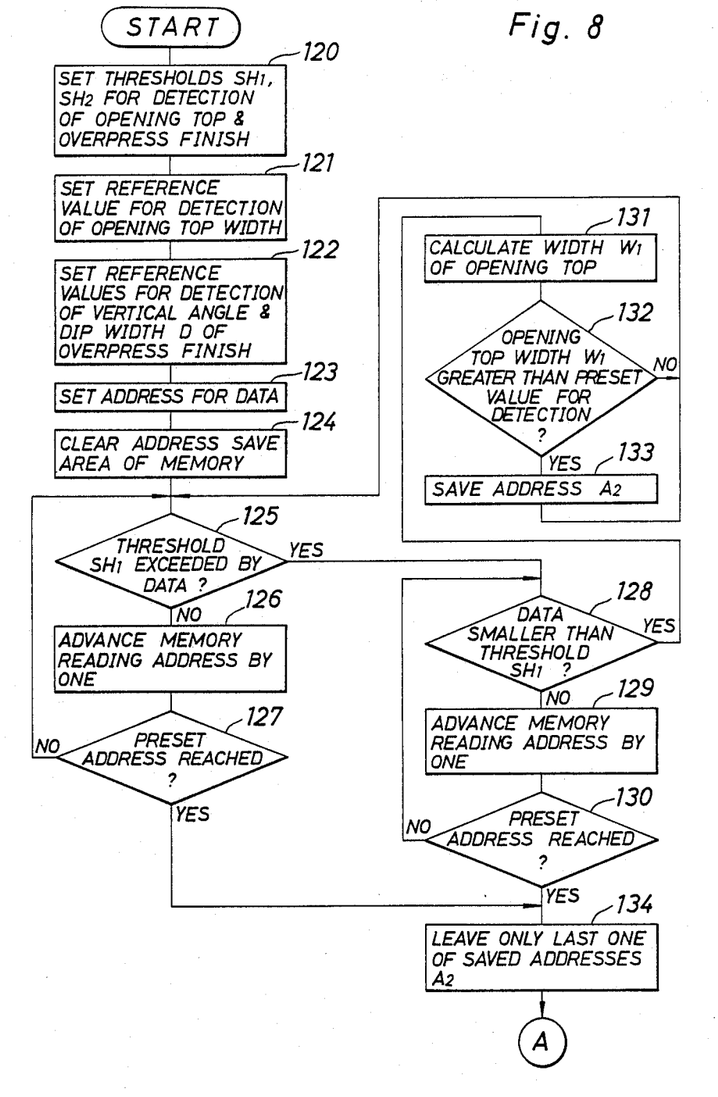
FIGS. 8, 9 and 10 are flow charts illustrating an opening top detecting operation, an overpress finish detecting operation and an acceptance judging operation, respectively.
Figure 9:
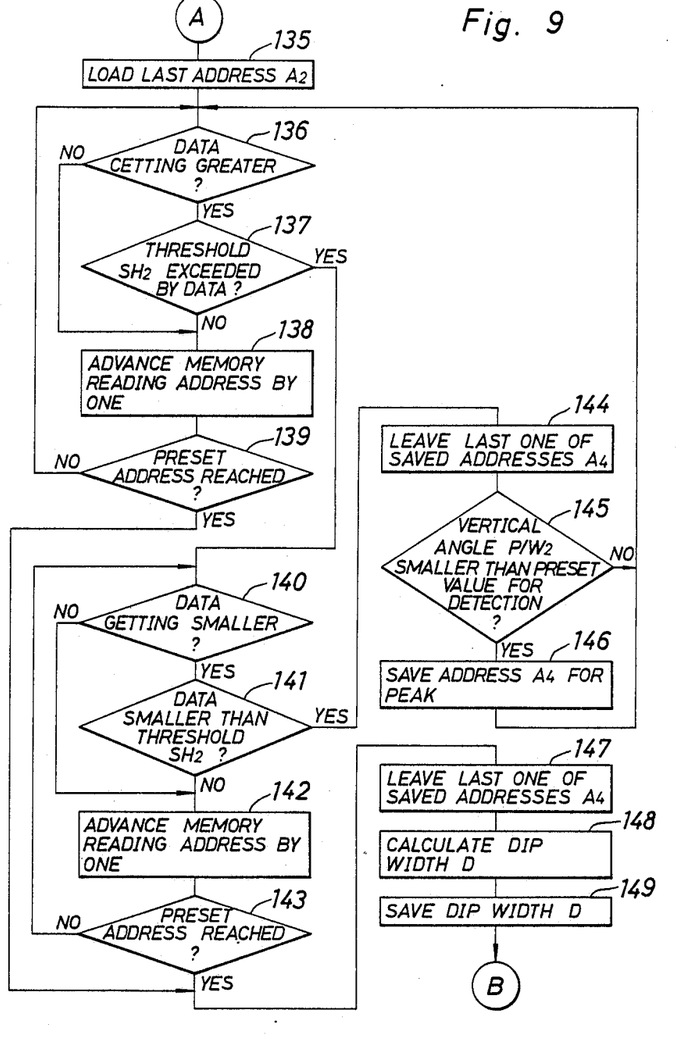
Figures 10, 11:
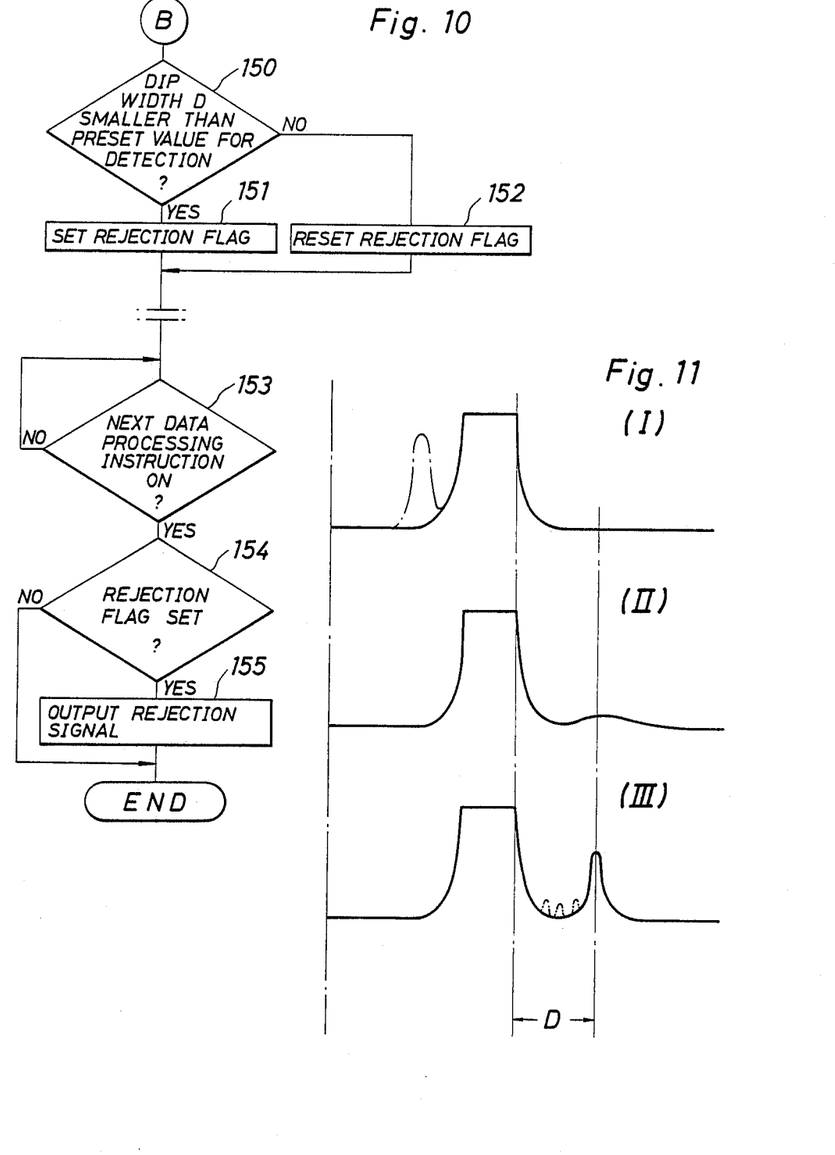
FIG. 11 is a waveform diagram illustrating an output of the linear image sensor.

The detection of rejection at step 113 is concretely effected as illustrated in flow charts of FIGS. 8, 9 and 10. However, in prior to description of the flow charts, a criterion in such detection will be described.

It is already mentioned that if data taken in from the linear image sensor 5 are represented in analog amounts, they will be such as shown in FIG. 3. In the present embodiment, in order to at first detect an opening top 2 itself, a threshold $SH_1$ for output voltages of the cells 10 of the linear image sensor 5 is determined, and thus the output voltages of the cells 10 are compared one after another with the threshold $SH_1$ in an order of the cells 10 in a direction from the outer side toward the inner side of the opening top 2. Here, the number of the cells 10 the output voltages of which exceed the threshold $SH_1$ (the number of the cells from an address $A_1$ to another address $A_2$) is determined as a width $W_1$ of the opening top 2 of the bottle 1, and only when the width $W_1$ is greater than a predetermined value (a reference value for inspection), a subsequent next step for detection of an overpress finish will take place.

An output of the linear image sensor 5 where a bottle 1 is normal is indicated by a waveform of a solid line in (I) of FIG. 11. In case there is a flange finish, for example, at an outer circumference of the opening top 2, a waveform as shown by a chain line in (I) of FIG. 11 will appear corresponding thereto, but this is ignored in the present embodiment.

Detection of an overpress finish 3 is effected by the cells 10 following the address $A_2$. Thus, a threshold $SH_2$ is determined, and the number of the cells 10 the output voltages of which exceed the threshold $SH_2$ (that is, the number of the cells from an address $A_3$ to another address $A_5$) is determined as the length $W_2$ of the bottom side of the overpress finish 3. Then, the quotient $P/W_2$ of the length $W_2$ to the height $P$ of a peak of the overpress finish 3 is found out and is determined as the vertical angle of the overpress finish 3, and when it is lower than a predetermined value, presence of an overpress finish is determined.

Accordingly, when there is a gentle projection formed on an inner circumference of the opening top 2, the output of the linear image sensor 5 will be such as shown in (II) of FIG. 11 and since the vertical angle is great, absence of an overpress finish (acceptable product) is determined.

In case of presence of an overpress finish, a width D of a dip between a peak of the overpress finish and an edge of the opening top 2 (that is, the number of the cells from the address $A_2$ to another address $A_4$) is found out, and if the dip width D is higher than a predetermined value, the bottle 1 is finally determined as a rejected product. An output of the linear image sensor 5 in this case is illustrated in (III) of FIG. 11.

Accordingly, an overpress finish with which the dip width D is smaller than the predetermined value as shown in a chain line in (III) of FIG. 11 is ignored.

The reason why acceptance or rejection is finally determined from the magnitude of the dip width D is that as far as an overpress finish 3 formed at an inner circumference of an opening top 2 of a bottle 1 is concerned, the magnitude of the dip width D is actually porportional to the degree of rejection of the product.

FIG. 8 illustrates a flow chart for detecting an opening top 2 of a bottle 1 where initialization of the system is first effected, including step 120 ... determine thresholds $SH_1$, $SH_2$ for detections of an opening top and an overpress finish step 121 ... determine a reference value for detection of a width of an opening top step 122 ... determine reference values for detections of the vertical angle and a dip width D of an overpress finish step 123 ... determine an address for data step 124 ... clear an address save area of the memory. After then, for each of data recalled from the cells of the memory 6a or 6b, testing of step 125 ... does the data exceed the threshold $SH_1$?

is effected, and if the results of the test at step 125 are NO, operation of step 126 ... advance the reading address of the memory by one is effected, whereafter testing of step 127 ... is the specified address reached? is effected. If the results of the test here are NO, control returns to step 125 to repeat similar operations for a subsequent next address. On the other hand, if the threshold $SH_1$ is exceeded, that is, if the results of the test at step 125 are turned over to YES, control goes to step 128 ... is the data lower than the threshold $SH_1$?

If the results are NO at step 128, operation of step 129 ... advance the reading address of the memory by one is effected, and then a test of step 130 ... is the specified address reached? is effected. If the results of the test are NO here, control returns to step 128 to repeat similar operations for a subsequent next address.

On the other hand, if the data is lower than the threshold $SH_1$, that is, if the results of the test at step 128 are turned over to YES, control goes to step 131 ... calculate a width $W_1$ of the opening top so that the width $W_l$ is determined from a difference between an address $A_1$ for which the threshold $SH_1$ is first exceeded at step 125 and another address $A_2$ for which the data first becomes lower than the threshold $SH_1$ at step 128. After then, testing of step 132 ... is the width $W_1$ of the opening top greater than the reference value for detection?

is effected. If the results of the test at step 132 is NO, then control returns immediately to step 125, but on the contrary if the judgment is YES, control returns to step 125 after operation of step 133 ... save the address $A_2$.

If the results are turned over to YES at step 127 or 130 (such detection of an opening top of a bottle as described above is repeated until the specified address is reached), an overpress finish detecting routine as illustrated in FIG. 9 is effected after operation of step 134 . . . leave only the last one of saved addresses $A_2$.

Referring now to FIG. 9, operation of step 135 . . . load the last address $A_2$ is first effected, and then for data of addresses following the address $A_2$, testing of step 136 . . . does the data have an increasing tendency ?

is first effected. If the results of the test are YES, another test of step 137 . . . is the data higher than the threshold $SH_2$ ?

is effected, and here if the results are NO, control goes, after operation of stpe 138 . . . advance the reading address of the memory by one, to step 139 . . . is the specified address reached ? Here, if the results of the test are NO, control returns to step 136 to repeat similar operations for a subsequent next address. On the contrary, if the results at step 136 are NO, control skips step 137 and directly goes to step 138.

On the other hand, if the threshold $SH_2$ is exceeded, that is, if the results of the test at step 137 are turned over to YES, then testing of step 140 . . . does the data have a decreasing tendency ?

is effected. Here, if the results are YES, control goes to step 141 . . . is the data smaller than the threshold $SH_2$ ?

If the results of the test at step 141 is NO, operation of step 142 . . . advance the reading address of the memory by one is effected, and then testing of step 143 . . . is the specified address reached ? is effected. Here, if the results are NO, control returns to step 140 to repeat similar operations for a subsequent next address. On the other hand, when the results of the test at step 140 are YES, then control skips step 141 and directly goes to step 142.

It is to be noted that at steps 136, 137, 140 and 141 and at steps 125 and 128 of FIG. 8, an average value of a predetermined plurality of addresses is found, and comparison is effected with reference to the average value.

Meanwhile, if the results of the test at step 141 are turned over to YES, control goes to step 144 . . . calculate the vertical angle $P/W_2$ of the overpress finish so that the length $W_2$ of the bottom side of the overpress finish is determined from an address $A_3$ for which the threshold $SH_2$ is exceeded at step 137 and another address $A_5$ for which the data first becomes lower than the threshold $SH_2$ at step 141 and then the height P of a peak between the addresses $A_3$ and $A_5$ is found whereafter the quotient $P/W_2$ is calculated. After then, testing of step 145 . . . is the vertical angle smaller than the reference value for inspection ?

is effected, and here if the results are NO, control returns directly to step 136, but on the contrary in case of YES, control returns to step 136 after step 146 . . . save the address $A_4$ corresponding to the peak.

If the results are turned over to YES at step 139 or 143, operations of step 147 . . . leave the last one of the addresses $A_4$ saved step 148 . . . calculate a width D of a dip are effected in order so that the dip width D is determined from a difference of the addresses $A_2$ and $A_4$ left in a manner as described above, whereafter control goes to an acceptance judging routine of FIG. 10 after operation of step 149 . . . save the dip width D. Referring now to FIG. 10, testing of step 150 . . . is the dip width D greater than the specified value for rejection ? is effected first, and here if the results are YES, operation of step 151 . . . set a rejection flag is effected, but n the contrary if the results of the test at step 150 are NO, operation of step 152 . . . reset a rejection flag is effected. In either case, testing of step 153 . . . is a next data treating instruction on ? is effected. If the results of the test here are YES, control goes to step 154 . . . is the rejection flag set ? and if the results are YES, it is followed by an operation of step 155 . . . output a rejection signal.

The rejection signal is inputted to the exclusion driver 20 shown in FIG. 4. Upon reception of the rejection signal, the exclusion driver 20 provides an excluding output as shown in FIG. 6 so that an unacceptable bottle is excluded in a known manner.

Figure 12:
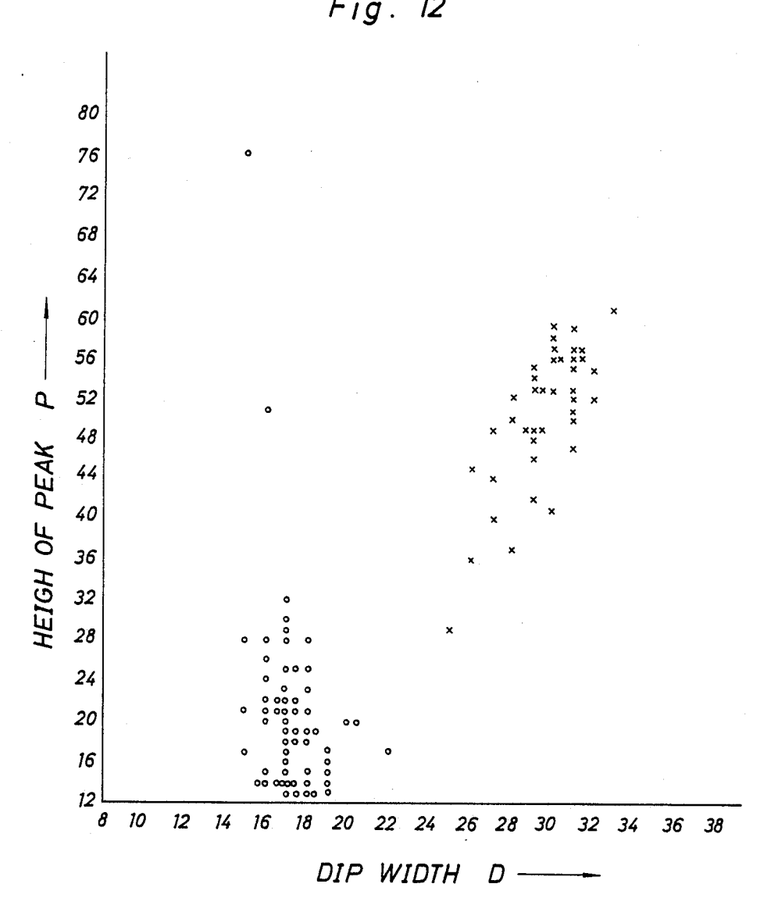
FIGS. 12, 13 and 14 are diagrams indicating that a width of a dip between an edge of an opening top and an overpress finish is differentiated between acceptable and unacceptable products in various arrangements according to the invention.

In the present embodiment, as shown in FIG. 2, light from the projector 4 is projected obliquely to an opening top 2 of a bottle 1 from the inside toward the outside of the opening of the bottle 1, and reflected light from the opening top 2 is received by the linear image sensor 5 on the outside of an area of the opening of the bottle 1. The reason is that such a relation between the projected light and the reflected light would assure distinct appearance of a difference in the dip width D as a result of comparison between acceptable and unacceptable products. FIG. 12 is a diagram illustrating actually measured data of the dip width D, and in this figure, a symbol o indicates an acceptable product while x indicates an unacceptable or rejected product. In the diagram of FIG. 12, the abscissa indicates the dip width D (each numeral indicates the number of cells of the linear image sensor), and the ordinate indicates the height P of peaks of overpress finishes (each numeral indicates one 256th of a voltage of 10 volts).

Figure 13:
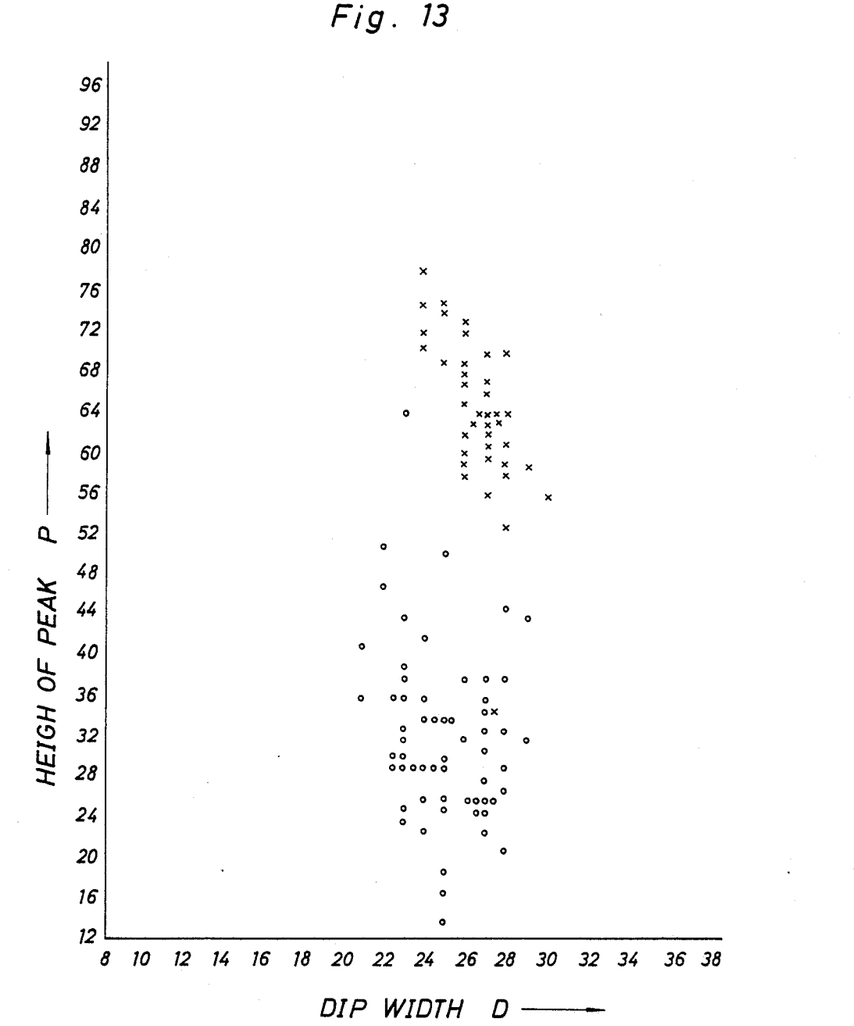
Figure 14:
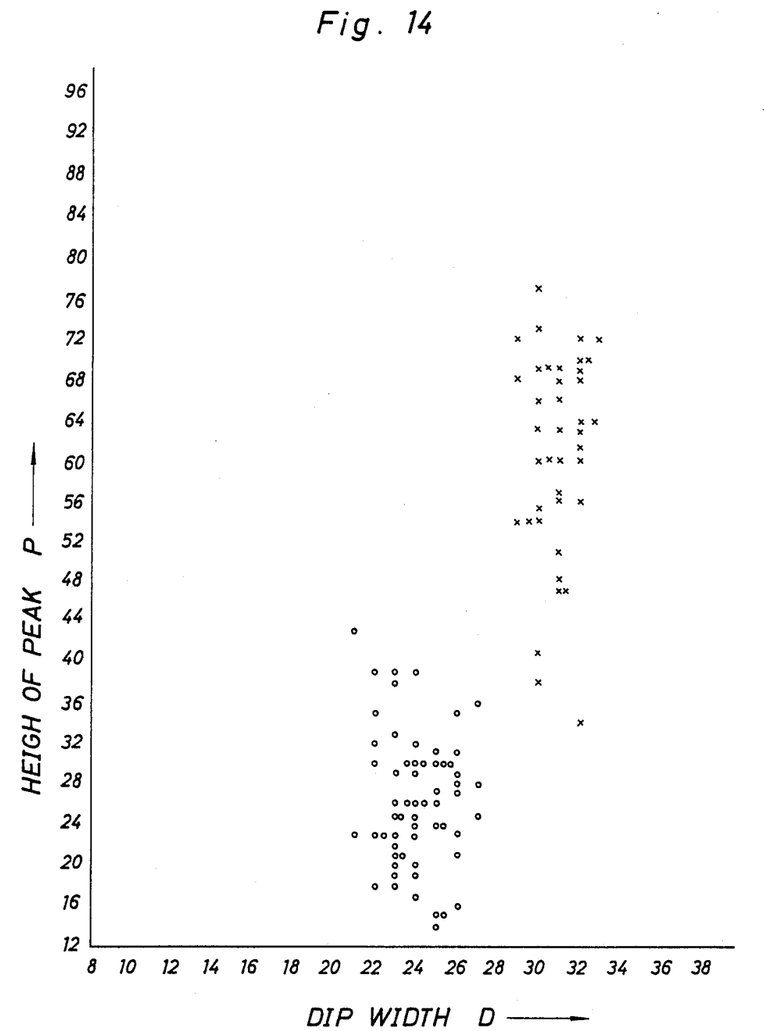

Meanwhile, FIG. 13 illustrates actually measured data where a relation between projected light and reflected light is reversed to that of the present embodiment, that is, light is projected obliquely from the outside to the inside of an opening region of an opening top 2 of a bottle 1 and is thus received at a position inside of the same, while FIG. 14 illustrates actually measured data where projected light and reflected light extend along a tangential line of a circumference of an opening top 2 of a bottle 1. It is to be noted that the incident angle $\theta_1$ and the reflecting angle $\theta_2$ relative to the opening top 2 are about 75 degrees in each of FIGS. 12, 13 and 14.

As can be seen from comparison of those three figures, FIG. 12 indicates a more distinct difference between acceptable and rejected products than FIGS. 13 and 14. However, it is to be understood that the present invention is not limited to a relation between projected light and reflected light as illustrated in FIG. 12 but includes such relations as illustrated in FIGS. 13 and 14 within the scope thereof.

It is to be noted that while in the embodiment described the digital amounts stored in the memories 6a and 6b are scanned in an order of the addresses in a direction from the outside to the inside of an opening top 2 of a bottle 1, judgment may otherwise be done in the reverse order. Further, while a product is judged to be accepted or rejected based on the magnitude of the dip width D after presence or absence of an overpress finish 3 has been judged from the vertical angle $P/W_2$ of the overpress finish 3, it may otherwise be judged only from the magnitude of the height P of a peak of an overpress finish 3. Meanwhile, while an opening top 2 of a bottle 1 is detected from the magnitude of the width thereof, it is apparent from FIGS. 12, 13 and 14 that it can otherwise be detected from the magnitude of the height thereof. In addition, while an image sensor of the linear type is employed, it may be replaced by an image sensor of the matrix type. Further, the present invention can also be applied to any other vessel than a bottle.

As apparent from the foregoing description, according to the present invention, light reflected from an opening top of a vessel is received by an image sensor and outputs of cells of the image sensor are stored as digital amounts individually into cells of a memory specified by corresponding addresses whereafter the digital amounts are judged one after another to detect the opening top and then the digital amounts are judged one after another for addresses after such detection to detect presence or absence of an overpress finish depending upon the magnitude of the digital amounts. According, presence or absence of an overpress finish can be detected accurately.

What is claimed is:

1. A method of inspecting a lip of a vessel, said method comprising the following steps:

projecting light to a lip of said vessel which is in position for inspection;

receiving light reflected from the lip of the vessel along a width of the lip using an image sensor;

storing outputs of individual cells of the image sensor as digital signals in cells of corresponding addresses of a memory in an order of increasing address, including a first address ($A_1$), which is less than a second address ($A_2$), which is less than a third address ($A_3$), which is less than a fourth address ($A_4$), which is less than a fifth address ($A_5$);

recalling the stored digital signals one after another from the memory in said order and comparing the recalled stored digital signals with a first threshold value ($SH_1$) to determine the width ($W_1$) of the lip of the vessel in accordance with a number of those of said cells of said memory between said first address ($A_1$) to said second address ($A_2$) which exceed said first threshold value;

comparing said width with a first predetermined value;

if said width is greater than said first predetermined value, recalling the stored digital signals in order from said memory beginning with said second address and comparing the recalled stored digital signals with a second threshold value ($SH_2$) which is less than said first threshold value to determine a length ($W_2$) of an overpress finish with the number of those of said cells of said memory from said third address to said fifth address which exceed said second threshold value;

detecting said fourth address of that one of said cells of said memory containing the recalled stored digital signal which has the largest value (P) of those between said third and fifth addresses;

extracting said largest value (P) from said memory at said fourth address;

calculating a ratio between said largest value and the length of the overpress finish and detecting a vertical angle of the overpress finish in accordance with said ratio;

comparing said vertical angle with a second predetermined value;

if said vertical angle is smaller than said second predetermined value, detecting a width (D) of a dip in accordance with a number of said cells in said memory between said second and fourth addresses;

comparing said dip width with a third predetermined value; if said dip width is greater than said third predetermined value, outputting a signal indicating that said vessel is to be rejected.

* * * * *